(12) United States Patent
Ueno et al.

(10) Patent No.: US 9,763,868 B2
(45) Date of Patent: Sep. 19, 2017

(54) SKIN COLLAGEN PRODUCTION-PROMOTING AGENT

(71) Applicant: MEGMILK SNOW BRAND CO., LTD., Hokkaido (JP)

(72) Inventors: Hiroshi Ueno, Hokkaido (JP); Yoshikazu Morita, Hokkaido (JP); Aiko Ono, Hokkaido (JP); Ken Katoh, Hokkaido (JP); Noriko Ueda, Hokkaido (JP)

(73) Assignee: MEGMILK SNOW BRAND CO., LTD., Hokkaido (JP)

( * ) Notice: Subject to any disclaimer, the term of this patent is extended or adjusted under 35 U.S.C. 154(b) by 0 days.

(21) Appl. No.: 14/863,477

(22) Filed: Sep. 24, 2015

(65) Prior Publication Data

US 2016/0015618 A1   Jan. 21, 2016

Related U.S. Application Data

(62) Division of application No. 13/982,012, filed as application No. PCT/JP2012/052690 on Feb. 7, 2012, now abandoned.

(30) Foreign Application Priority Data

Feb. 9, 2011 (JP) ................................. 2011-026446

(51) Int. Cl.

| | |
|---|---|
| *A61K 8/64* | (2006.01) |
| *A61K 8/67* | (2006.01) |
| *A61Q 19/00* | (2006.01) |
| *A61K 38/18* | (2006.01) |
| *A23L 2/66* | (2006.01) |
| *A61Q 19/08* | (2006.01) |
| *A23L 2/02* | (2006.01) |
| *A23L 2/52* | (2006.01) |
| *A61K 38/01* | (2006.01) |
| *A23L 33/17* | (2016.01) |
| *A23L 33/175* | (2016.01) |
| *A23L 33/18* | (2016.01) |
| *A23L 33/19* | (2016.01) |

(52) U.S. Cl.
CPC *A61K 8/64* (2013.01); *A23L 2/02* (2013.01); *A23L 2/52* (2013.01); *A23L 2/66* (2013.01); *A23L 33/17* (2016.08); *A23L 33/175* (2016.08); *A23L 33/18* (2016.08); *A23L 33/19* (2016.08); *A61K 8/676* (2013.01); *A61K 38/018* (2013.01); *A61K 38/1841* (2013.01); *A61Q 19/00* (2013.01); *A61Q 19/007* (2013.01); *A61Q 19/08* (2013.01); *A23V 2002/00* (2013.01); *A61K 2800/592* (2013.01); *A61K 2800/74* (2013.01)

(58) Field of Classification Search
None
See application file for complete search history.

(56) References Cited

U.S. PATENT DOCUMENTS

| | | | |
|---|---|---|---|
| 3,794,722 A | 2/1974 | Taya | 424/647 |
| 5,420,243 A | 5/1995 | Ogawa et al. | |
| 5,461,033 A | 10/1995 | Donnet et al. | |
| 5,658,883 A | 8/1997 | Ogawa et al. | |
| 6,506,732 B1 | 1/2003 | Amiot | |
| 6,974,796 B1* | 12/2005 | Girsh | A61K 31/726 424/9.1 |
| 8,247,435 B2* | 8/2012 | Thornthwaite | A61K 31/122 424/615 |
| 2006/0247162 A1 | 11/2006 | Morita et al. | |
| 2008/0113433 A1 | 5/2008 | Robins et al. | |
| 2008/0268534 A1 | 10/2008 | Robins et al. | |
| 2009/0004160 A1 | 1/2009 | Park et al. | |
| 2009/0048145 A1 | 2/2009 | Hellerbrand et al. | |
| 2010/0135941 A1 | 6/2010 | Watanabe et al. | |
| 2010/0183682 A1 | 7/2010 | Nakao | 424/275.1 |

(Continued)

FOREIGN PATENT DOCUMENTS

| | | |
|---|---|---|
| EP | 0 353 772 | 2/1990 |
| EP | 0 527 283 | 2/1993 |

(Continued)

OTHER PUBLICATIONS

Pancreatin, in MeSH Database, National Center for Biotechnology Information, Bethesda, Maryland, USA [online], [retrieved on Nov. 13, 2016]. Retrieved from the Internet: <URL: http://www.ncbi.nlm.nih.gov/mesh/68010194>.*

Trypsin, in MeSH Database, National Center for Biotechnology Information, Bethesda, Maryland, USA [online], [retrieved on Nov. 13, 2016]. Retrieved from the Internet: <URL: http://www.ncbi.nlm.nih.gov/mesh/68014357>.*

Chymotrypsin, in MeSH Database, National Center for Biotechnology Information, Bethesda, Maryland, USA [online], [retrieved on Nov. 13, 2016]. Retrieved from the Internet: <URL: http://www.ncbi.nlm.nih.gov/mesh/68002918>.*

(Continued)

*Primary Examiner* — David Romeo

(74) *Attorney, Agent, or Firm* — Greenblum & Bernstein, P.L.C.

(57) ABSTRACT

A problem of the present invention is to provide a skin collagen production-promoting agent without safety problems. Another problem of the present invention is to provide a skin collagen production-promoting food or drink product and a skin collagen production-promoting cosmetic product containing such a substance. TGF-β and/or a TGF-β degradation product, which is acquired by degrading TGF-β with a protease such as pepsin, pancreatin, etc., are used as a skin collagen production-promoting agent or the active ingredient of a skin collagen production-promoting food or drink product and a skin collagen production-promoting cosmetic product. The aforementioned TGF-β and/or TGF-β degradation product have an effect of increasing the collagen content of the skin.

6 Claims, No Drawings

(56) References Cited

U.S. PATENT DOCUMENTS

| | | |
|---|---|---|
| 2013/0225497 A1 | 8/2013 | Kato et al. |
| 2013/0225501 A1 | 8/2013 | Kato et al. |
| 2013/0310318 A1 | 11/2013 | Ueno et al. |
| 2013/0338336 A1 | 12/2013 | Katoh et al. |

FOREIGN PATENT DOCUMENTS

| | | |
|---|---|---|
| EP | 2 138 159 | 12/2009 |
| JP | 2-167231 | 6/1990 |
| JP | 5-284936 | 11/1993 |
| JP | 6-25288 | 2/1994 |
| JP | 8-510443 | 11/1996 |
| JP | 2003-144095 | 5/2003 |
| JP | 2004-254674 | 9/2004 |
| JP | 2008-501455 | 1/2008 |
| JP | 2009-524425 | 7/2009 |
| JP | 2009-528034 | 8/2009 |
| WO | 2010/006412 | 1/2010 |

OTHER PUBLICATIONS

Pepsin A, in MeSH Database, National Center for Biotechnology Information, Bethesda, Maryland, USA [online], [retrieved on Nov. 13, 2016]. Retrieved from the Internet: <URL: http://www.ncbi.nlm.nih.gov/mesh/?term=Pepsin+A>.*
Papain, in MeSH Database, National Center for Biotechnology Information, Bethesda, Maryland, USA [online], [retrieved on Nov. 13, 2016]. Retrieved from the Internet: <URL: http://www.ncbi.nlm.nih.gov/mesh/68010206>.*
Kalllikreins, in MeSH Database, National Center for Biotechnology Information, Bethesda, Maryland, USA [online], [retrieved on Nov. 13, 2016]. Retrieved from the Internet: <URL: http://www.ncbi.nlm.nih.gov/mesh/68007610>.*
Cathepsins, in MeSH Database, National Center for Biotechnology Information, Bethesda, Maryland, USA [online], [retrieved on Nov. 13, 2016]. Retrieved from the Internet: <URL: http://www.ncbi.nlm.nih.gov/mesh/68002403>.*
Thermolysin, in MeSH Database, National Center for Biotechnology Information, Bethesda, Maryland, USA [online], [retrieved on Nov. 13, 2016]. Retrieved from the Internet: <URL: http://www.ncbi.nlm.nih.gov/mesh/68013820>.*
Glutamyl endopeptidase, in MeSH Database, National Center for Biotechnology Information, Bethesda, Maryland, USA [online], [retrieved on Nov. 13, 2016]. Retrieved from the Internet: <URL: http://www.ncbi.nlm.nih.gov/mesh/67028344>.*
Takehara, "Growth regulation of skin fibroblasts", Journal of Dermatological Science, vol. 24, Suppl. 1, 2000, pp. S70-S77.
Jin et al., "Separation, Purification, and Sequence Identification of TGF-$\beta$1 and TGF-$\beta$2 from Bovine Milk", Journal of Protein Chemistry, vol. 10, No. 5, 1991, pp. 565-575.
International Preliminary Report on Patentability for PCT/JP2012/052690, mailed Aug. 22, 2013.
International Search Report for PCT/JP2012/052690, mailed Apr. 3, 2012.
Rossert et al., "Regulation of type I collagen genes expression", *Nephrol. Dial. Transplant.*, vol. 15, Suppl. 6, pp. 66-68 (2000).
Verrecchia, "Interactions fonctionnelles entre la voie de signalisation du TGF-$\beta$ par les Smads et le TNF-$\alpha$: implications dans la régulation de l'expression du collagène de type I", *Journal de la Société de Biologie*, vol. 199, No. 4, pp. 329-336 (2005), including an English-language abstract.
Brenner et al., "Fibrogenesis and type I collagen gene regulation", *J. Lab. Clin. Med.*, vol. 124, No. 6, pp. 755-760 (1994).
Database WPI, Week 200373, Thomson Scientific, London, GB, AN 2003-771361—&JP 2003-144095, May 20, 2003.
Extended European Search Report for EP Patent Application No. 12744857.9, mailed Jan. 12, 2015.
Yin et al., "The Crucial Role of TGF-$\beta$ in the Age-Related Alterations Induced by Ultraviolet A Irradiation", *The Journal of Investigative Dermatology, Letters to the Editor*, vol. 120, No. 4 , pp. 703-705, 2003.
Ozawa et al., "Transforming Growth Factor-$\beta$ Activity in Commercially Available Pasteurized Cow Milk Provides Protection against Inflammation in Mice", *The Journal of Nutrition*, vol. 139, pp. 69-75, published online Dec. 3, 2008.
Mukherjee et al., "Retinoids in the Treatment of Skin Aging: An Overview of Clinical Efficacy and Safety", *Clinical Interventions in Aging*, vol. 1, No. 4, pp. 327-348, 2006.
Taiwanese Office Action, dated Mar. 6, 2015.
Akpek G. Clinical grading in chronic graft-versus-host disease: is it time for change? Leuk Lymphoma. Jun. 2002;43(6):1211-20.
Chen et al., "Stimulation of Type I Collagen Transcription in Human Skin Fibroblasts by TGF-$\beta$: Involvement of Smad 3", *J. Invest. Dermatol.* 112(1):49-57, 1999.

* cited by examiner

SKIN COLLAGEN PRODUCTION-PROMOTING AGENT

CROSS-REFERENCE TO RELATED APPLICATIONS

This application is a Divisional of U.S. patent application Ser. No. 13/982,012, which is the National Stage of PCT/JP2012/052690, filed Feb. 7, 2012, which claims priority to Japanese Patent Application No. 2011-026446, filed Feb. 9, 2011. The disclosures of each of U.S. patent application Ser. No. 13/982,012 and PCT/JP2012/052690 are expressly incorporated by reference herein in their entireties.

TECHNICAL FIELD

The present invention relates to a skin collagen production-promoting agent, a skin collagen production-promoting food or drink product, and a skin collagen production-promoting cosmetic product useful for preventing skin deterioration such as roughening, wrinkles, and the loss of elasticity in the skin. Particularly, the present invention relates to a skin collagen production-promoting agent comprising transforming growth factor-beta (TGF-β) and/or a TGF-β degradation product acquired by degrading TGF-β with a protease as an active ingredient.

BACKGROUND ART

As a result of recent advancement in researches on the mechanism of skin deterioration, it has been confirmed that, macroscopically speaking, the feeling of skin dryness and the roughening of the skin are not only caused by the decline of metabolism due to aging but also intricately involved with the effect of factors such as sunlight (ultraviolet), drying, and oxidation. It has been revealed that collagen fibers, which are the most primal matrix components of the dermis, are significantly reduced by the effect of these factors. Wrinkles and sagging of the skin are increased if the machinery for retaining the tension of the skin, such as resilience and elasticity, supported by the collagen fibers is destroyed due to the effect of the factors such as ultraviolet. Since collagen can hold water in molecules thereof and thereby helps to keep the skin moisturized, if collagen is destroyed by an external factor, the skin is dried and roughened. From the above, a skin collagen production-promoting agent is desired that can prevent wrinkles and sagging of the skin by promoting the biosynthesis of collagen, which is one of the major components of the dermic layer, without safety problems.

Transforming growth factor beta (TGF-β) is one of the growth factors present in the milk of mammals. The TGF-β family includes five subtypes, which are proteins forming a dimer of about 25 kDa by disulfide bonds. The TGF-β family has a function of regulating the promotion/inhibition of cell proliferation, biosynthesis, differentiation, and apoptosis. The effect of inducing differentiation in animal cells has been confirmed as a useful effect of TGF-β (Patent Document 1). TGF-β is also reported as a growth factor of fibroblast cells in the skin (Non-Patent Literature 1).

CITATION LIST

Patent Literature

Patent Document 1: Japanese Laid-Open Patent Publication No. 2004-254674

Non Patent Literature

Non-Patent Literature 1: J. Dermatol. Sci., Vol. 24 (Supple), p. 70, 2000

SUMMARY OF INVENTION

Technical Problem

A problem of the present invention is to provide a skin collagen production-promoting agent without safety problems. Another problem of the present invention is to provide a skin collagen production-promoting food or drink product and a skin collagen production-promoting cosmetic product containing such a substance.

Solution to Problem

As a result of extensive search for a substance producing a skin collagen production-promoting effect contained in various food materials in order to solve the problems, the inventers found that TGF-β or a TGF-β degradation product acquired by degrading TGF-β increases collagen content in the skin, thereby completing the present invention.

The present invention includes the following embodiments.

(1) A skin collagen production-promoting agent comprising TGF-β and/or a TGF-β degradation product as an active ingredient.

(2) The skin collagen production-promoting agent of (1), wherein the TGF-β degradation product is acquired by degrading TGF-β with a protease.

(3) The skin collagen production-promoting agent of (2), wherein the protease is one or more selected from trypsin, pancreatin, chymotrypsin, pepsin, papain, kallikrein, cathepsin, thermolysin, and V8 protease.

(4) The skin collagen production-promoting agent of any one of (1) to (3), wherein the TGF-β degradation product has an average molecular weight of 500 or more and 8,000 or less.

(5) A skin collagen production-promoting food or drink product comprising the TGF-β and/or the TGF-β degradation product of any one of (1) to (4).

(6) A skin collagen production-promoting cosmetic product comprising the TGF-β and/or the TGF-β degradation product of any one of (1) to (4).

(7) A method of improving skin quality by oral ingestion of or application of TGF-β and/or a TGF-β degradation product.

(8) A method of improving skin quality by oral ingestion of 10 μg per day or more of TGF-β and/or a TGF-β degradation product or application thereof at 0.001 to 2 wt %.

(9) A method of promoting production of collagen in the skin comprising administering TGF-β and/or a TGF-β degradation product.

(10) The method of promoting production of collagen in the skin of (9), wherein the TGF-β degradation product is acquired by degrading TGF-β with a protease.

(11) The method of promoting production of collagen in the skin of (10), wherein the protease is one or more selected from trypsin, pancreatin, chymotrypsin, pepsin, papain, kallikrein, cathepsin, thermolysin, and V8 protease.

(12) The method of promoting production of collagen in the skin of any one of (9) to (11), wherein the TGF-β degradation product has an average molecular weight of 500 or more and 8,000 or less.

(13) A method of preventing or improving skin deterioration comprising administering TGF-β and/or a TGF-β degradation product.

(14) The method of preventing or improving skin deterioration of (13), wherein the TGF-β degradation product is acquired by degrading TGF-β with a protease.

(15) The method of preventing or improving skin deterioration of (14), wherein the protease is one or more selected from trypsin, pancreatin, chymotrypsin, pepsin, papain, kallikrein, cathepsin, thermolysin, and V8 protease.

(16) The method of preventing or improving skin deterioration of any one of (13) to (15), wherein the TGF-β degradation product has an average molecular weight of 500 or more and 8,000 or less.

(17) A skin deterioration-preventing or -improving agent comprising TGF-β and/or a TGF-β degradation product as an active ingredient.

(18) The skin deterioration-preventing or -improving agent of (17), wherein the TGF-β degradation product is acquired by degrading TGF-β with a protease.

(19) The skin deterioration-preventing or -improving agent of (18), wherein the protease is one or more selected from trypsin, pancreatin, chymotrypsin, pepsin, papain, kallikrein, cathepsin, thermolysin, and V8 protease.

(20) The skin deterioration-preventing or -improving agent of any one of (17) to (19), wherein the TGF-β degradation product has an average molecular weight of 500 or more and 8,000 or less.

(21) A skin deterioration-preventing or -improving food or drink product comprising the TGF-β and/or the TGF-β degradation product of any one of (17) to (20).

(22) A skin deterioration-preventing or -improving cosmetic product comprising the TGF-β and/or the TGF-β degradation product of any one of (17) to (20).

(23) A method of improving skin quality for purely cosmetic purposes by oral ingestion of or application of TGF-β and/or a TGF-β degradation product.

(24) A method of improving skin quality for purely cosmetic purposes by oral ingestion of 10 μg per day or more of TGF-β and/or a TGF-β degradation product or application thereof at 0.001 to 2 wt %.

Advantageous Effects of Invention

The present invention provides a skin collagen production-promoting agent, a skin collagen production-promoting food or drink product, and a skin collagen production-promoting cosmetic product containing TGF-β and/or a TGF-β degradation product as an active ingredient. The skin collagen production-promoting agent, the skin collagen production-promoting food or drink product, and the skin collagen production-promoting cosmetic product have an effect of promoting collagen production in the skin and are useful for the prevention and treatment of wrinkles, sagging, feeling of dryness, and roughening of the skin.

DESCRIPTION OF EMBODIMENTS

A feature of the skin collagen production-promoting agent of the present invention is that TGF-β and/or a TGF-β degradation product acquired by degrading TGF-β with a protease is contained as an active ingredient. TGF-β of any origin is usable in the present invention. For example, human- and bovine-derived TGF-βs have gene sequences already revealed and can be produced with gene recombination, and TGF-β produced with a genetic engineering technique is usable in the present invention. TGF-β is contained in a relatively large amount in bovine colostrum and may be collected from the milk. TGF-β is also collectable from the medium of cell culture and such cell-derived TGF-β is also usable. For example, milk-derived TGF-β is producible in accordance with a known method (see, e.g., *J. Protein Chem.*, Vol. 10, pp. 565-575, 1991), and TGF-β can be acquired from raw milk, powdered milk, skim milk, reconstituted milk, or other processed milk by heat treatment, salting treatment, ethanol treatment, various chromatographic processes such as ion exchange chromatography and gel filtration chromatography, and an ultrafiltration process in a combined manner as needed.

For the TGF-β degradation product, a peptide mixture is usable that is acquired by limited proteolysis of TGF-β with a protease such as trypsin, pancreatin, chymotrypsin, pepsin, papain, kallikrein, cathepsin, thermolysin, and V8 protease to an average molecular weight of 8,000 or less. Meanwhile, the lower limit of the average molecular weight is preferably equal to or greater than 500. For example, the average molecular weight of the TGF-β degradation product is 500 or more and 8000 or less, 1500 or more and 8000 or less, 2500 or more and 8000 or less, 3500 or more and 8000 or less, 4500 or more and 8000 or less, 5500 or more and 8000 or less, 6500 or more and 8000 or less, 7500 or more and 8000 or less, 500 or more and 7500 or less, 1500 or more and 7500 or less, 2500 or more and 7500 or less, 3500 or more and 7500 or less, 4500 or more and 7500 or less, 5500 or more and 7500 or less, 6500 or more and 7500 or less, 500 or more and 6500 or less, 1500 or more and 6500 or less, 2500 or more and 6500 or less, 3500 or more and 6500 or less, 4500 or more and 6500 or less, 5500 or more and 6500 or less, 500 or more and 5500 or less, 1500 or more and 5500 or less, 2500 or more and 5500 or less, 3500 or more and 5500 or less, 4500 or more and 5500 or less, 500 or more and 4500 or less, 1500 or more and 4500 or less, 2500 or more and 4500 or less, 3500 or more and 4500 or less, 500 or more and 3500 or less, 1500 or more and 3500 or less, 2500 or more and 3500 or less, 500 or more and 2500 or less, 1500 or more and 2500 or less, or 500 or more and 1500 or less.

The skin collagen production-promoting agent of the present invention is orally administered or applied to produce the skin collagen production-promoting effect. When the skin collagen production-promoting agent of the present invention is orally administered, the active ingredient, i.e., TGF-β or a TGF-β degradation product may directly be used or may be formulated in a usual manner and used as an oral agent such as powders, granules, tablets, capsules, and drinkable preparations. In the present invention, for example, oral agents such as powders, granules, tablets, and capsules are formulated in a usual manner by using excipients such as starch, lactose, sucrose, mannitol, carboxymethylcellulose, corn starch, and inorganic salts. This kind of formulation can be achieved by using the excipients as well as pharmaceutical additives such as binders, disintegrating agents, surfactants, lubricants, fluidity promoters, coloring agents, and flavors as needed. More specifically, binding agents include, for example, starch, dextrin, gum arabic, gelatin, hydroxypropyl starch, sodium carboxymethyl cellulose, methylcellulose, crystalline cellulose, ethyl cellulose, and polyvinyl pyrrolidone. Disintegrating agents include, for example, starch, hydroxypropyl starch, carboxymethyl cellulose, sodium carboxymethyl cellulose, cross-linked sodium carboxymethyl cellulose, and crystalline cellulose. Surfactants include soybean lecithin, sucrose fatty acid ester, etc.; lubricants include talc, wax, sucrose fatty acid ester, hydrogenated vegetable oil, etc.; and fluidity promoters include anhydrous silicic acid, dried aluminum hydroxide, magnesium silicate, etc.

TGF-β or a TGF-β degradation product may be combined with nutrients, food or drink etc., directly or after formulated into preparations. If TGF-β or a TGF-β degradation product is contained together with a component conventionally considered to be effective in collagen production, such as vitamin C, a further skin collagen production-promoting effect can be expected. Since TGF-β or a TGF-β degradation product is relatively stable to heat, raw materials containing TGF-β or a TGF-β degradation product can be heat-sterilized under the normally used conditions.

When the skin collagen production-promoting agent of the present invention is applied, the skin collagen production-promoting agent can be combined with known normally used components depending on the purpose of use and prepared as various dosage forms such as liquid formulation, solid formulation, and semisolid formulation and preferable compositions include ointment, gel, cream, spray, patches, lotion, powder, etc. For example, the skin collagen production-promoting agent of the present invention can be mixed with hydrocarbons such as vaseline, stearyl alcohol, higher fatty acid lower alkyl ester such as isopropyl myristate, animal oil and fat such as lanolin, polyhydric alcohol such as glycerin, glycerin fatty acid ester, mono-stearic acid, surfactants such as polyethylene glycol, inorganic salt, wax, resin, water, and, if needed, preservatives such as methyl parahydroxybenzoate and butyl parahydroxybenzoate, so as to produce skin collagen production-promoting cosmetics and pharmaceutical agents.

Although an effective oral administration dose of the skin collagen production-promoting agent of the present invention is not constant and is prescribed as needed depending on the drug formulation, the administration method, the purpose of use, and the age, body weight, and disease condition of the patient to which the promoter is administered, it was found as a result of animal experiments using rats that the skin collagen production-promoting effect can be expected to be produced by ingesting 10 µg per one kilogram of rat body weight or more of TGF-β and/or a TGF-β degradation product. Therefore, according to the extrapolation method, the effect can be expected by ingesting 10 µg per adult human or more of TGF-β and/or a TGF-β degradation product daily and, thus, TGF-β and/or a TGF-β degradation product may be combined with food or drink or administered as a medical drug so that this required amount can be ensured. The administration can be performed several times per day in a divided manner as needed.

Although an effective application dose of the skin collagen production-promoting agent of the present invention varies depending on the dosage form, TGF-β and/or a TGF-β degradation product may preferably be contained to be 0.001 to 2 wt % based on the total dosage of the composition to be applied. However, if the composition is diluted upon use as in the case of bath additives, the contained amount may further be increased.

EXAMPLES

The present invention will hereinafter be described in detail with reference to examples and test examples; however, these examples only exemplarily illustrate embodiments of the present invention and the present invention is not limited by these examples.

Example 1

After a column packed with 3,000 gram of S-Sepharose was sufficiently washed with deionized water and 10,000 liter of skim milk was allowed to flow therethrough, the column was sufficiently washed with deionized water before elution with a linear concentration gradient of 0.1 to 1.0 M sodium chloride. An elution fraction containing TGF-β was fractionated again with phenyl-S Sepharose hydrophobic column chromatography. This fraction was further sequentially processed by C4 and C8 reverse phase chromatography and gel filtration chromatography in an HPLC system to acquire 412 mg of TGF-β (fraction A). TGF-β acquired in this manner is directly usable as the skin collagen production-promoting agent.

Example 2

After 25 mg of the fraction A acquired in Example 1 was suspended in 100 ml of water, pancreatin was added at the final concentration of 1% to perform enzyme treatment at 37° C. for 5 minutes to 6 hours. After heat treatment was performed at 90° C. for 5 minutes to inactivate the enzyme, 24 mg of TGF-β degradation products (fractions B, C, and D) was acquired by lyophilization. The average molecular weights of the TGF-β degradation products B, C, and D acquired in this manner were about 8,000, about 500, and about 300, respectively. The fractions B and C are directly usable as the skin collagen production-promoting agent.

Test Example 1

The collagen production-promoting effects of the fraction A acquired in Example 1 and the fractions B to D acquired in Example 2 were examined by animal experiments using rats. Seven-week-old Wistar male rats were divided into nine test groups (n=6) consisting of a group administered saline (control group), a group administered 10 µg per one kilogram of rat body weight of the fraction A acquired in Example 1 (A-1 group), a group administered 100 µg per one kilogram of rat body weight of the fraction A acquired in Example 1 (A-2 group), groups administered 10 µg per one kilogram of rat body weight of the fractions B to D acquired in Example 2 (B-1 to D-1 groups), and groups administered 100 µg per one kilogram of rat body weight of the fractions B to D acquired in Example 2 (B-2 to D-2 groups), and each of the rats received oral administration once a day with a probe and was fed for 10 days. With regard to the collagen content in the skin, after treating the dermis of the rats in accordance with the method of Nimni et al., (see *Arch. Biochem. Biophys.*, p. 292, 1967), hydroxyproline content in the soluble fraction was measured. Since hydroxyproline is a specific amino acid contained only in collagen and accounts for about 10% of the total amino acid constituting collagen, collagen content can be estimated (see Ryuji Asano et al., *Bio Industry*, p. 12, 2001). The results are shown in Table 1.

TABLE 1

| | Hydroxyproline content (µg/ml) |
|---|---|
| Control group | 0.3 ± 0.1 |
| A-1 group | 0.7 ± 0.1* |
| A-2 group | 1.1 ± 0.2 |
| B-1 group | 0.6 ± 0.1* |
| C-1 group | 0.7 ± 0.2* |
| D-1 group | 0.5 ± 0.1* |
| B-2 group | 1.0 ± 0.3* |
| C-2 group | 1.1 ± 0.2* |
| D-2 group | 0.6 ± 0.2* |

Each numerical value is a mean ± standard deviation (n = 6).
*A significant difference exists as compared to the control group ($p < 0.05$).

As a result, the hydroxyproline content in the soluble fraction after 10 weeks indicated significantly higher values in all the test groups as compared to the control group. Therefore, it was clarified that TGF-β and a TGF-β degradation product having an average molecular weight of 500 or more and 8,000 or less have the skin collagen production-promoting effect and are useful as a skin collagen production-promoting agent. It was also clarified that the skin collagen production-promoting effect is observed when TGF-β and a TGF-β degradation product are administered in an amount of at least 10 μg per one kilogram of rat body weight.

Test Example 2

The collagen production-promoting effects of the fraction A acquired in Example 1 and the fraction B acquired in Example 2 were examined by experiments using a human fibroblast cell line [CCD45SK (ATCCRL 1506) collected from the skin of Caucasian women]. The normal human fibroblast cell line was seeded onto a 24-well plate at $4 \times 10^4$ cells/well/0.4 ml by using a modified Eagle's medium (MEM, 10-101, Dainippon Pharmaceutical Co., Ltd.) containing 10 vol % fetal bovine serum (hereinafter abbreviated as FBS), cultured with 5% carbon dioxide under saturated water vapor at 37° C. for 24 hours, and then replaced to a 0.6 vol % FBS-containing MEM medium. The fraction A acquired in Example 1 and the fraction B acquired in Example 2 were added to each well (0.1 vol % final) (n=6) and cultured for 24 hours, and β-aminopropionitrile and tritium-L-proline were then added (50 μg/ml and 1 μCi/ml final, respectively), to acquire culture medium after further culturing for 24 hours. From the culture medium acquired in this manner, collagen fractions were fractionated in accordance with the method of Webster et al., (see, *Analytical Biochemistry*, p. 220, 1979) to measure radioactivity incorporated into the collagen fractions. The same test was conducted as a control without adding TGF-β and the TGF-β degradation product. The results are shown in Table 2.

TABLE 2

|  | Collagen production (%) |
| --- | --- |
| Control | 100 ± 3 |
| Fraction A | 204 ± 11* |
| Fraction B | 215 ± 9* |

Each numerical value is a mean ± standard deviation (n = 6).
*A significant difference exists as compared to the control group ($p < 0.05$).

The results indicate that all the groups with TGF-β and the TGF-β degradation product added exhibited a collagen production-promoting ability twice or more greater than the group without the addition of TGF-β and the TGF-β degradation product (control). Therefore, it was clarified that TGF-β and a TGF-β degradation product have an effect on the skin fibroblast cells to promote collagen production and are useful as a skin collagen production-promoting agent.

Example 3

Skin collagen production-promoting drink having composition shown in Table 3 was manufactured in a usual manner. Flavor of the manufactured drink was favorable and did not deteriorate after storage for one year at room temperature, and there was no problem such as precipitation.

TABLE 3

| Mixed isomerized sugar | 15.0 (wt %) |
| --- | --- |
| Fruit juice | 10.0 |
| Citric acid | 0.5 |
| Fraction A (product of Example 1) | 0.1 |
| Flavors | 0.1 |
| Mineral mixture | 0.1 |
| Water | Added to a total amount of 100.0 |

Example 4

Dough having composition shown in Table 4 was prepared, shaped, and baked in a usual manner to manufacture skin collagen production-promoting biscuits.

TABLE 4

| Flour | 50.0 (wt %) |
| --- | --- |
| Sugar | 20.0 |
| Salt | 0.5 |
| Margarine | 12.5 |
| Egg | 12.5 |
| Water | 3.5 |
| Mineral mixture | 0.8 |
| Fraction C (product of Example 2) | 0.2 |

Example 5

Skin collagen production-promoting agent having composition shown in Table 5 was manufactured in a usual manner.

TABLE 5

| Dextrose monohydrate | 90.5 (wt %) |
| --- | --- |
| Mineral mixture | 5.0 |
| Fraction A (product of Example 1) | 3.0 |
| Sugar ester | 1.0 |
| Flavors | 0.5 |

Example 6

Skin lotion having composition shown in Table 6 was manufactured in a usual manner.

TABLE 6

| Glycerin | 3.0 (wt %) |
| --- | --- |
| 1,3-butylene glycol | 3.0 |
| Polyoxyethylene sorbitan monooleate (20 E.O.) | 0.5 |
| Methyl parahydroxybenzoate | 0.15 |
| Citric acid | 0.1 |
| Sodium citrate | 1.0 |
| Flavors | 0.05 |
| Fraction B (product of Example 2) | 0.05 |
| Purified water | Added to a total amount of 100.0 |

Example 7

Cream having composition shown in Table 7 was manufactured in a usual manner.

TABLE 7

| Liquid paraffin | 5.0 (wt %) |
| --- | --- |
| White beeswax | 4.0 |
| Cetanol | 3.0 |
| Squalane | 10.0 |
| Lanolin | 2.0 |
| Stearic acid | 1.0 |
| Polyoxyethylene sorbitan monooleate (20 E.O.) | 1.5 |
| Glyceryl monostearate | 3.0 |
| 1,3-butylene glycol | 6.0 |
| Methyl parahydroxybenzoate | 1.5 |
| Flavors | 0.1 |

TABLE 7-continued

| | |
|---|---|
| Fraction A (product of Example 1) | 0.5 |
| Purified water | Added to a total amount of 100.0 |

Test Example 3

The skin lotion acquired in Example 6 and the cream acquired in Example 7 were used for a practical use test. Comparison products were used that had the same compositions as Examples 6 and 7 except that TGF-β and the TGF-β degradation product were removed. Twenty adult women having dry skin with sagging and fine wrinkles recognized on the facial surfaces were randomly divided into two groups of 10 each (groups E and F) and twenty women with roughening of skin recognized on the hands were randomly divided into two groups of 10 each (groups G and H) to apply 2 g of the skin lotion of the preset invention to the facial surfaces of the group E, 2 g of the skin lotion of the comparison product to the facial surfaces of the group F, 2 g of the cream of the preset invention to the fingers of the group and 2 g of the cream of the comparison product to the fingers of the group H, twice a day in a similar manner to the normal usage condition for 10 days. The results are shown in Table 8.

TABLE 8

| | Feeling of dryness | Roughening of the skin | Wrinkles | Sagging |
|---|---|---|---|---|
| Group E | ++ | ++ | ++ | + |
| Group F | ± | ± | ± | ± |
| Group G | ++ | + | ND | ND |
| Group H | ± | ± | ND | ND |

++: A prominent improvement effect was observed after application for 10 days.
+: An improvement effect was observed after application for 10 days.
±: No improvement effect was observed after application for 10 days (no change occurred from 10 days ago).
ND: Not determined From Table 8, it was clarified that prominent improvement effects were exhibited especially for feeling of dryness and roughening of the skin in the groups E and G using the skin lotion of the product of Example 6 and the cream of the product of Example 7, as compared to the groups F and H using the skin lotion and the cream of the comparison products.

What is claimed is:

1. A method of increasing the collagen content in the skin of a subject comprising orally administering a TGF-β degradation product to a subject in recognized need thereof in an amount effective to increase the collagen content in the skin of the subject,
    wherein the TGF-β degradation product is acquired by degrading TGF-β with pancreatin, and
    wherein the TGF-β degradation product has an average molecular weight of 500 or more and 8,000 or less.

2. A method of increasing the collagen content in the skin of a subject comprising orally administering 10 µg per day or more of a TGF-β degradation product to a subject in recognized need thereof to increase the collagen content in the skin of the subject,
    wherein the TGF-β degradation product is acquired by degrading TGF-β with pancreatin, and
    wherein the TGF-β degradation product has an average molecular weight of 500 or more and 8,000 or less.

3. The method according to claim 1, which comprises orally administering said TGF-β degradation product in combination with vitamin C.

4. The method according to claim 2, which comprises orally administering said TGF-β degradation product in combination with vitamin C.

5. The method according to claim 1, wherein the TGF-β degradation product has an average molecular weight of 1500 or more and 6500 or less.

6. The method according to claim 2, wherein the TGF-β degradation product has an average molecular weight of 1500 or more and 6500 or less.

* * * * *